United States Patent [19]

Turecek

[11] Patent Number: 5,432,062
[45] Date of Patent: Jul. 11, 1995

[54] METHOD OF PROTEOLYTICALLY CLEAVING PROTHROMBIN TO PRODUCE THROMBIN

[75] Inventor: Peter Turecek, Vienna, Austria

[73] Assignee: Immuno Aktiengesellschaft, Vienna, Austria

[21] Appl. No.: 40,261

[22] Filed: Mar. 30, 1993

[30] Foreign Application Priority Data

Apr. 6, 1992 [AU] Australia .................................. 712/92

[51] Int. Cl.$^6$ ..................... C12P 21/06; C12N 9/74; A61K 32/43
[52] U.S. Cl. ................. 435/68.1; 435/214; 424/94.64
[58] Field of Search .............. 435/68.1, 214; 424/94.64; 530/384

[56] References Cited

U.S. PATENT DOCUMENTS

| | | | |
|---|---|---|---|
| 2,495,298 | 1/1950 | Szentbyorgyi et al. | 435/214 |
| 4,210,580 | 7/1980 | Amrani | 530/383 |
| 4,380,511 | 4/1983 | Mannuzza et al. | 435/214 |
| 4,703,001 | 10/1987 | Vodian et al. | 435/5 |
| 5,143,838 | 9/1992 | Kraus et al. | 435/214 |
| 5,151,355 | 9/1992 | Crowley et al. | 435/214 |
| 5,158,873 | 10/1992 | Abbott et al. | 435/26 |
| 5,200,340 | 4/1993 | Foster et al. | 424/94.64 |

FOREIGN PATENT DOCUMENTS

| | | |
|---|---|---|
| 20457/92 | 2/1993 | Australia . |
| 0328229 | 8/1989 | European Pat. Off. . |
| 0369817 | 5/1990 | European Pat. Off. . |
| 3834550 | 4/1990 | Germany . |
| WO93/07276 | 4/1993 | WIPO . |

OTHER PUBLICATIONS

Stroud (1974) *Sci. Am.*, 231(1), 74–88.
Neurath (1984) *Science*, 224, 350–357.
Esmon (1987) *Science*, 235, 1348–1352.
Sawyer et al. (1973) *J. Biol. Chem.*, 248(24), 8429–8433.
Benyon et al., Eds, *Proteolytic Engmes: A Practical Approach*, p. 111 (Oxford University Press, 1989).
Abstract of International Application No. WO 93/05187 (published: Mar. 1993).
Abstract of German Application No. 3834550 (published Apr. 1990).

*Primary Examiner*—Marian C. Knode
*Assistant Examiner*—Jon P. Weber
*Attorney, Agent, or Firm*—Foley & Lardner

[57] ABSTRACT

Prothrombin is cleaved by proteases in the presence of a detergent or certain chaotropic substances to produce thrombin. Under these conditions, controlled and restricted proteolysis occurs such that significant activation without digestion occurs. The chaotropic substances may be urea, guanidinium hydrochloride or a thiocyanate salt. Reversible immobilization of prothrombin on a solid support prior to activation improves the selectivity of the proteolytic activation.

12 Claims, 2 Drawing Sheets

METHOD OF PROTEOLYTICALLY CLEAVING PROTHROMBIN TO PRODUCE THROMBIN

BACKGROUND OF THE INVENTION

The invention relates to a method for the controlled, limited proteolytic cleavage of proteins, in particular proenzymes, for recovering enzymes and protein fragments, respectively, wherein the protein is treated with a protease. In particular, the invention relates to a method of recovering thrombin from prothrombin.

Such a method has been known from EP-A-0 378 798. According to that method, prothrombin derived from plasma or a plasma fraction is adsorbed on a solid carrier (immobilized), and the adsorbate is treated with $Ca^{2+}$ ions. The $Ca^{2+}$ ions are used in concentrations up to 30 mM and, together with the proteases also derived from the plasma and adsorbed on the carrier, cause the thrombin to be cleaved from the adsorbate. As the solid carrier, methacrylic and acrylic copolymers are used.

It has furthermore been known that trypsin degrades dissolved prothrombin into fragments of low molecular weight, wherein a complete loss of the thrombin activity is to be found (Biochim. Biophys. Act. 329, 221-232 (1973)); the proteolytic degradation of the prothrombin thus does not end with thrombin, and thus this method does not lend itself to the recovery of thrombin.

All the methods of the initially defined kind lead to different prothrombin cleavage products, depending on the protease and treatment conditions used, which cleavage products in part may be used therapeutically (e.g. thrombin) and in part may be used diagnostically and for the recovery of specific antibodies. For all these applications it is, however, necessary that the protein fragments are highly pure, which necessarily involves a lot of work, since all the known cleavage methods lead to a plurality of fragments. A further disadvantage of these multi-stage and time-consuming purification methods is that they necessarily involve high losses of yield.

SUMMARY OF THE INVENTION

The invention aims at eliminating these disadvantages and has as its object to provide an improved method of recovering enzymes or protein fragments from proteins, wherein this method is to be particularly suited for the simple recovery of thrombin.

With the method of the initially defined kind, this object is achieved in that the treatment with the protease is effected in the presence of a detergent or in the presence of a chaotropic substance, with the exception of coagulatively active salts.

The invention is based on the finding that the proteolytic cleavage of proteins, in particular of proenzymes, such as prothrombin, takes place on purpose or can be controlled if it is carried out in the presence of a detergent or in the presence of a chaotropic substance. It has been shown that the cleavage pattern of the proteins is different depending on the type and concentration of these substances present. This finding opens up the possibility of selecting the reaction environment such that only a few and precisely selected protein fragments are formed.

A preferred variant of the method of the invention consists in that a proenzyme is used which has been immobilized on a solid carrier material, in particular on a hardly soluble salt or chelate of a bivalent metal, preferably of an alkaline earth metal. This variant allows for an easier recovery of the protein fragment cleaved from the adsorbed proenzyme, since the part of the proenzyme, adsorbed to the carrier, simply may be separated from the reaction solution with the carrier.

DETAILED DESCRIPTION

Figure 1:
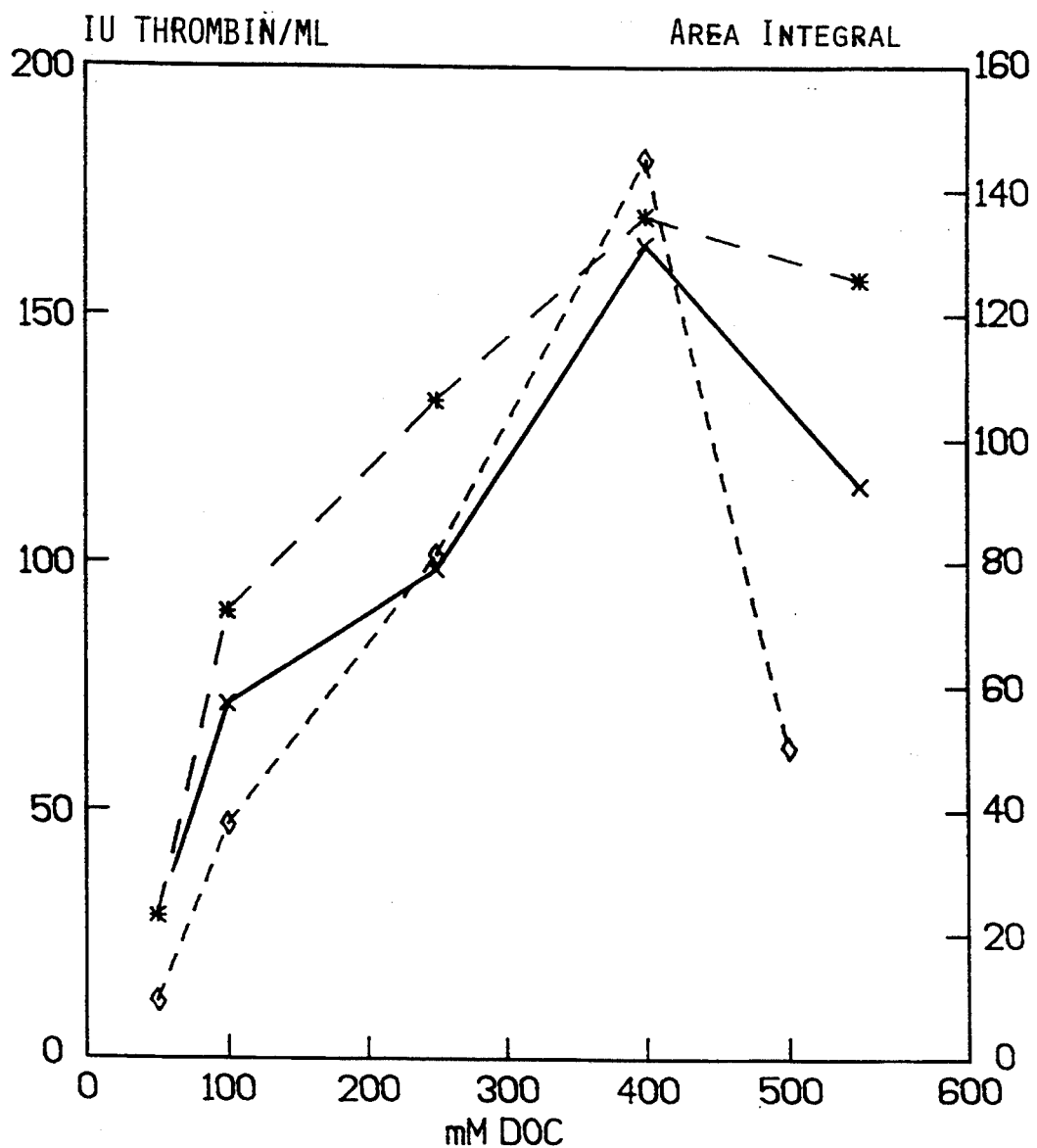
FIG. 1. The effect of added deoxycholate (DOC) on the yield of active thrombin.

According to the method described in EP-A-0 378 798 copolymers are used as the carriers, which, however, have the disadvantage that they could release acrylic and methacrylic monomers into the thrombin-containing solution which are difficult to remove again and thus contaminate the pharmaceutical preparation to be produced. Such a leakage has been known for all types of organic polymeric carriers. It has, however, been shown that the inventive controlled cleavage of a proenzyme, in particular prothrombin, succeeds not only on copolymers, but also on other carriers, e.g. on hardly soluble salts, such as $Ca_3(PO_4)_2$, $CaSO_4$, $CaCO_3$, $BASO_4$, $BaCO_3$ or barium citrate. The salts may either be added to a prothrombin-containing solution, or they may be newly formed by precipitation of a prothrombin-containing solution.

A particular advantage of the bivalent ions of the carrier is further that they selectively bind prothrombin via their gamma-carboxy-glutamic acid terminus. On account of the missing gamma-carboxy-glutamic acid terminus, the protein fragments forming during the proteolytic treatment of the prothrombin have no affinity to bivalent ions and thus to the carrier.

As further carriers, also hydroxylapatite, a hydroxylapatite gel or a metal chelate-affinity chromatographic carrier loaded with a bivalent cation (e.g. Pharmacia Chelating Sepharose ®) are suited.

A plurality of proteases (e.g. chymotrypsin, dispase, endopeptidase Arg-C, endoproteinase Lys-C, endoproteinase Glu-C, endoproteinase Asp-N, factor Xa, kallikrein, papain, pepsin, plasmin, pronase, proteinase K, staphylocoagulase, subtilisin, thrombin, trypsin (in particular human, bovine, porcine), trypsin-like proteases from arthropods or microorganisms, such as e.g. *Streptomyces griseus*—trypsin, serine-proteases from venomous snakes, like *Angkistrodon rhodostoma*, *Bothrops atrox*, *Dispholidus typus*, *Echis carinatus*, *Naja nigrocollis*, *Oxyuranus scutellatus scutellatus*, and others) lend themselves to the proteolytic cleavage of proenzymes. Trypsin, chymotrypsin, kallikrein, dispase or the endoproteinase Glu-C, Lys-C or Asp-N, are preferably used as the protease. Recombinant proteases may be used as well.

It has been shown that in the presence of a detergent a proenzyme may be cleaved so selectively that the enzyme to be recovered forms the main portion of the fragment mixture. Deoxycholate (DOC), which preferably is used, is suitable as the detergent, and also other substances, such as dodecylsulfate (SDS), CHAPS, polyoxyethylene derivatives, such as Brij ®, Tween ®, Triton ® and Pluronic ®, are suitable. The presence of the detergent further facilitates the desorption of the protein-fragments formed, from the carrier.

Typical chaotropic substances applied in the method according to the invention are, e.g., urea, guanidinium hydrochloride as well as thiocyanates, yet coagulatively active salts, such as, e.g., calcium salts, which also act chaotropically, are not suitable.

The supernatant obtained, which contains the desired enzyme, may be subjected to further purification steps. Advantageously, gel permeation chromatography or affinity chromatography may be used therefor. To obtain samples as concentrated as possible, the use of affinity chromatographic methods is recommended. Dye ligand affinity chromatographic carriers with ligands of the Cibacron®-Blue F3GA-type (produced by Ciba Geigy) or Procion®-Red HE-3B (produced by ICI) or related dyes have proved to be suitable. The protein fragments may be adsorbed on the respective affinity matrix (e.g. Fractogel® TSK AF-Blue (produced by Merck), Blue-Sepharose® CL-6B (produced by Pharmacia) in the batch or in the packed column directly from the desorption supernatant after the solid phase activation has taken place. Subsequently the protein fragments are separated from the detergent by washing with a buffer and finally eluted with a highly molar (e.g. 1M) chaotropic substance (e.g. KSCN or $NH_4SCN$).

The eluate may be freed from the chaotropic substance by gel permeation chromatography (e.g. via Sephadex® G25), diafiltration or dialysis and may be brought into a suitable buffer or a salt solution. Further purification to homogenicity may be effected in a known manner via reverse phase chromatography, affinity chromatography or gel permeation chromatography.

The method according to the invention is particularly suitable for obtaining pure thrombin. Therefore, the invention also relates to the production of a thrombin-containing pharmaceutical preparation, wherein a preferred embodiment is characterised in that a prothrombin-containing solution is contacted with a solid carrier, in particular with a hardly soluble salt or a chelate of a bivalent metal, preferably of an alkali earth metal, so as to immobilize prothrombin on the carrier, the immobilized prothrombin is treated with a protease, in particular trypsin, in the presence of a detergent, preferably deoxycholate, so as to obtain a thrombin-containing solution that is separated and purified, and is processed to a pharmaceutical preparation.

It has been found that through the detergent treatment a marked reduction of virus activity is achieved, if a starting product is used which has come from a virus-contaminated pool. In one case it was found that no vaccinia viruses were detectable in a thrombin preparation produced according to the method of the invention, although the starting material (a fermentation supernatant) had contained vaccinia. Naturally, within the scope of the invention also additional measures can be taken to inactivate possibly present infectious agents, such as, e.g., a vapour-heat-treatment of a lyophilized product.

The inventive method of recovering thrombin suitably is carried out in the following manner:

At first, a prothrombin-containing solution is contacted with the solid carrier, so as to adsorb prothrombin. As the prothrombin-containing solution not only plasma or plasma fractions, but also recombinant prothrombin-containing cell culture supernatant medium may be used. After immobilization has been effected, the prothrombin bound to the carrier suitably is separated from the solution and washed so as to remove unspecifically bound proteins that might contaminate the later final product. Subsequently, the immobilized prothrombin is treated with the protease in the presence of deoxycholate so as to cleave the thrombin from the prothrombin, a thrombin-containing solution and a solid body being obtained, the solid body being separated from the solution. This is effected by sedimentation or by filtration.

The thrombin-containing supernatant may be subjected to the above described purification steps. It is preferred to carry out an affinity chromatography with Fractogel® TSK-AF Blue (Merck) with subsequent Sephadex®-G25 chromatography.

Subsequently, the pure thrombin-containing solution obtained optionally is concentrated by ultrafiltration or lyophilization and processed to a pharmaceutical preparation.

EXAMPLES

By the following Examples, the invention will be explained in more detail:

Preparation of the Immobilized Prothrombin

A cell culture supernatant medium according to PCT application WO 91/11519, which contains recombinant human prothrombin, is admixed with 5 g of powderized $Ca_3(PO_4)_2$ per 100 IU of prothrombin and is slightly stirred at 4° C. for one hour. Subsequently, the solid phase is centrifuged off at 5000 g, the pellet obtained is resuspended in 40 ml 20 mM Tris/HCl buffer (pH 7.4), stirred for 10 min and again centrifuged off at 5000 g. This procedure is repeated with 40 ml of 5% (W/V) ammonium sulfate in the above-mentioned buffer and finally with 40 ml of pure buffer.

In the same manner, e.g. a partial prothrombin complex, i.e. a mixture of factors II, IX and X, may be used as the prothrombin-containing starting material for preparing the immobilized prothrombin.

EXAMPLE 1

Influence of the Reaction Environment on the Tryptic Cleavage of the Immobilized Prothrombin To document the influence of chaotropic substances and detergents on the tryptic cleavage of prothrombin, at first four solutions (A–D) of a Tris/HCl buffer (20 mM; pH 8.3) were prepared with the following additions (the fourth buffer solution (D) served for comparison):

Solution A: urea (0.5M)
Solution B: Na-deoxycholate (0.05M)
Solution C: Na-dodecylsulfate (0.05M)
Solution D: no addition To 1 ml of solutions A–D subsequently 200 mg of buffer-moist, washed pellet (produced as described above) were each added and shaken at room temperature with 20 µl of a 20 mM Tris/HCl buffer containing 1 mg of trypsin/ml. After 1, 2 and 3 hours, aliquots of the suspension were each drawn, the solid phase was centrifuged off and the supernatants were examined for the respective fragment composition by means of Western blot analysis.

In Table 1, the peak area integrals of the fragment bands at 12, 19, 23, 25,5, 33, 35 and 44 kD after densitometric Western blot analysis are entered. It is apparent that tryptic fragments of different sizes can be detected in various amounts in dependence on the reaction environment selected. Contrary to the 3-hour incubation in pure Tris buffer (solution D), fragments in the molecule mass range above 30 kD remain in all the other solutions (A–C). The fragments at 33 kD and at 35 kD correspond to thrombin, 33 kD being associated with the active form.

In the presence of deoxycholate (solution B), active thrombin is formed as the main fragment, which furthermore is not decomposed to smaller oligopeptides even after a 3-hour treatment with trypsin.

TABLE 1

| Molecule mass(kD) | | 12 | 19 | 23 | 25,5 | 33 | 35 | 44 |
|---|---|---|---|---|---|---|---|---|
| Solution | Reaction time (h) | | | Peak Area Integral: | | | | |
| A | 1 | 26 | 19 | 22 | 14 | 94 | 95 | |
| | 2 | 22 | 20 | 13 | | 54 | 20 | |
| | 3 | 24 | 21 | 14 | | 51 | 17 | |
| B | 1 | | | 31 | | 165 | 90 | |
| | 2 | | 15 | | | 175 | 25 | |
| | 3 | | 18 | | | 170 | | |
| C | 1 | | | | | 53 | 11 | |
| | 2 | | | | | 35 | 2 | |
| | 3 | | | | | 9 | | |
| D | 1 | | 25 | 132 | | 117 | 22 | |
| | 2 | | 25 | 120 | | | 34 | |
| | 3 | | 42 | 129 | | | | |

EXAMPLE 2

Cleavage of Immobilized Prothrombin by Means of Various Proteases (In the Presence of a Detergent)

From a prothrombin-containing cell culture supernatant medium, prothrombin was adsorbed on $Ca_3(PO_4)_2$ and washed.

8 samples of 250 mg of buffer-moist adsorbate were each suspended in 1 ml of 20 mM Tris/HCl buffer, pH 8.3, containing 200 mM of Na-deoxycholate, and 50 µl of the following eight enzyme solutions were added thereto:
- kallikrein from porcine pancreas, 250 U/ml in 20 mM of TBS, pH 8.3,
- dispase I from *Bacillus polymyxa*, 1 mg/ml in 20 mM of TBS, pH 8.3,
- α-chymotrypsin from bovine pancreas, 350 U/ml in 20 mM of TBS, pH 8.3,
- trypsin from porcine pancreas, 0.76 mg/ml in 20 mM of TBS, pH 8.3,
- endoproteinase Glu-C from *Staphylococcus aureus* V8, 1 mg/ml in 20 mM of TBS, pH 8.3,
- endoproteinase Lys-C from *Lysobacter enzymogenes*, 0.1 mg/ml in 20 mM TBS, pH 8.3,
- endoproteinase Asp-N from *Pseudomonas fragi*, 0.04 mg/ml in 20 mM TBS, pH 8.3
- factor Xa, human, 20 U/ml The term 20 mM TBS (TBS=tris buffered saline) denotes a 20 mM tris-HCl-buffer (pH 8.3), which contains 0.9% NaCl.

The formulations were incubated for 2 hours at room temperature under shaking (20 hours in the case of kallikrein). Thereupon, aliquots of the formulations were admixed with SDS sample buffer (1:1) and examined for their fragment composition by means of Western blot analysis.

The peak area integrals of the fragment bands at 12, 18, 19, 20, 23, 33, 34, 35, 44, 47, 50, 52, 54, 55, 71 and 75 kD after densitometric Western blot analysis are given in Table 2.

It is apparent that a series of fragments in the molecule mass range of from 12 to 71 kD can be produced with the above-mentioned proteases. The fragment corresponding to active thrombin (33 kD) can be obtained in a particularly high yield by means of tryptic degradation of prothrombin.

TABLE 2

| Molecule mass (kD) | 12 | 18 | 19 | 20 | 23 | 33 | 34 | 35 | 44 | 47 | 50 | 52 | 54 | 55 | 71 | 75 |
|---|---|---|---|---|---|---|---|---|---|---|---|---|---|---|---|---|
| Protease | | | | | | Peak Area Integral | | | | | | | | | | |
| Kallikrein | | 12 | | 31 | | | | | | 15 | 16 | | 16 | | | 59 |
| Dispase | | | | | | | 36 | | | | | 27 | 8 | 39 | | |
| α-Chymotrypsin | | | | | | | 7 | 57 | | 9 | | | | 18 | 44 | |
| Trypsin | 20 | | | | | 14 | 56 | | | | | | | | | |
| Endoproteinase Glu-C | | 13 | 28 | | | 39 | | 17 | 13 | 17 | | | 78 | | | |
| Endoproteinase Lys-C | | | | | | | | | 6 | | 51 | | | | | 21 |
| Endoproteinase Asp-N | | | | | | 21 | 83 | | 11 | | | | 11 | | | 19 |
| Factor Xa | | | | | | | | 12 | 10 | | | | 31 | | | 98 |

EXAMPLE 3

Cleavage of Immobilized Prothrombin in the Presence of Deoxycholate in Various Concentrations As described above, at first recombinant prothrombin was adsorbed on $Ca_3(PO_4)_2$ from a fermentation supernatant.

5 samples of moist adsorbate of 0.6 g each were incubated for three hours at room temperature with 3 ml of 20 mM Tris/HCl buffer each, pH 8.3, containing Na-deoxycholate in the concentrations 50 mM, 100 mM, 250 mM, 350 mM and 500 mM, after the addition of 60 µl of a solution of 0.76 mg/ml of trypsin/ml under shaking. Thereupon the buffers of the media are changed against 0.9% NaCl. Then the samples were examined for their thrombin activity. Therein, the thrombin time in the coagulation test was determined with normal plasma and the amidolytic activity was determined with the chromogenic substrate TH-1 (2 AcOH.-D-CHG-ala-arg-p-nitroanilide) each photometrically, against an international thrombin standard (FIG. 1). FIG. 1 shows that the yield of active thrombin (33 kD-fragment) has a maximum at 350 mM deoxycholate.

Furthermore, it became apparent that the thrombin formed was not further degraded over a period of at least 20 hours despite the presence of trypsin.

Purification of Protein Fragments of the Cleaved Prothrombin 1.5 ml of a prothrombin fragment-containing solution derived in Example 3 (350 mM DOC) were adsorbed with 0.1% trifluoroacetic acid in $H_2O$ (solvent A) on a reverse phase HPLC column (Nucleosil 100-5C18, 125×4 mm) (flow rate: 1.7 ml/min). Thereupon it was eluted with 0.1% trifluoroacetic acid in acetonitrile (solvent B) with a linear gradient of from 30 to 70% B in 30 min at a flow rate of 1.7 ml/min. By detection at 220 nm 6 main peaks (retention times: 10.01 min; 11.96 min; 12.68 min; 13.47 min; 13.94 min; 14.47 min) could be identified; they were collected separately and lyophilized. Further analysis of the separated fragments was effected via SDS-PAGE with detection through Coomassie-staining, as well as by means of Western blot analysis with a polyclonal rabbit-anti-human prothrombin-antiserum. The molecule masses of the fragments were determined for the six main peaks with 9 kD, 16 kD, 21 kD, 23 kD, 12 kD and with 33 kD.

EXAMPLE 4

Recovery of Thrombin

A buffer-moist pellet (approximately 10 g) was incubated for one hour at room temperature and under slight stirring with 50 ml of a solution of 0.76 mg of porcine trypsin (Sigma T-0134) per ml in 20 mM Tris/HCl buffer (pH 8.3) which contained 200 mM of Na-deoxycholate. Thereafter, the calcium phosphate was separated by centrifugation. The supernatant contained primarily thrombin beside a few other fragments of prothrombin.

For purifying the supernatant, a column having a cross-sectional area of 8 cm$^2$ was packed with Fractogel ® TSK-AF Blue (Merck) at a height of 12 mm (gel volume—9.6 ml) in 20 mM of Tris/HCl buffer (pH 8.3) and washed with the same buffer. These and all subsequent steps were effected at 4° C.

The thrombin-containing supernatant (approximately 50 ml) was pumped over the gel at a flow rate of 2 ml/min to effect adsorption. Thereafter, unspecifically bound prothrombin fragments were eluted with 20 ml of 0.5 M NaCl solution, 40 ml of 1.0 M NaCl solution and 20 ml of 20 mM Tris/HCl buffer (pH 7.4) at a flow rate of 6 ml/min. In reverse flow direction, prothrombin fragments were then eluted at 1 ml/min with 20 mM Tris/HCl buffer, which contained 1M of KSCN. The eluate was photometrically measured via a flow cell at 280 nm, a total of 15 ml was collected.

Figure 2:
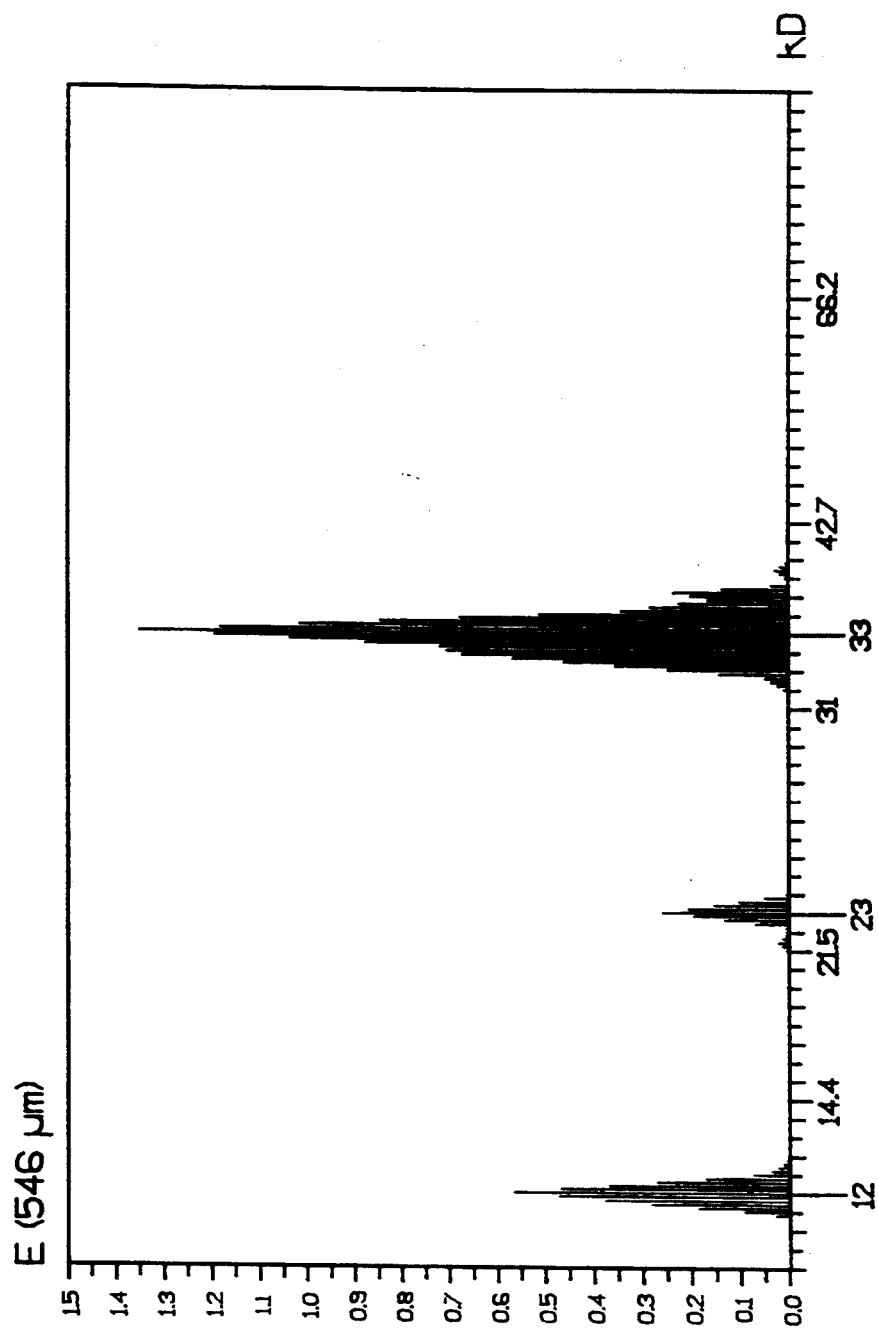
FIG. 2. Fragment composition of thrombin which has been activated by trypsin in the presence of deoxycholate.

The protein content of the eluate was 188 mg/ml according to Bradford. FIG. 2. shows the fragment composition (densitometric scan of Western blot) with dominant 33 kD-fragment (active thrombin). About 30% thereof are thrombin, based on the protein content. By determining the thrombin time, a specific activity of approximately 2200 IU/mg of protein could be determined for the thrombin. Thus, approximately 100 IU of thrombin could be obtained from 1 IU of prothrombin by tryptic solid phase activation.

The thrombin-containing solution obtained can be further purified in a known manner, concentrated and further processed to a pharmaceutical preparation.

EXAMPLE 5

Cleavage of Dissolved Prothrombin

Two samples of 1 ml each of prothrombin-containing fermentation supernatant were admixed with 1 ml of a 40 mM Tris/HCl buffer, pH 8.3, which contained 0.1M Na-deoxycholate and 0.1M Na-dodecyl sulfate, respectively, so that the detergent concentration in the solution amounted to 0.05M. For reasons of comparison, a third sample of 1 ml of prothrombin-containing fermentation supernatant was admixed with 40 mM Tris/HCl buffer without a detergent. After addition of 15 ml each of a solution of 1 mg trypsin/ml in 20 mM Tris/HCl buffer, pH 8.3, which contained 0.9% NaCl, it was incubated at room temperature for 4 hours under shaking.

After 1, 2, 3 and 4 hours, aliquots of the samples of 50 μl were each diluted with Laemmli-buffer (1:1), boiled and electrophoretically analyzed. The Western blot analysis of a 12% SDS polyacrylamide gel (1st antibody: anti-human-factor II rabbit serum; 2nd antibody: goat-anti-rabbit IgG peroxidase conjugate; developed by means of 4 chloro-1-naphtole) was densitometrically examined in the impinging light for quantifying the fragments. The results are entered in Table 3.

TABLE 3

| Addition | Reaction Time (h) | Molecule mass (kD) 19 | 25,5 | 33 | 35 |
|---|---|---|---|---|---|
| | | | Peak Area Integral | | |
| Deoxy- | 1 | | | 10 | |
| cholate | 2 | | | 9 | |
| | 3 | | | 7 | |
| | 4 | | | 6 | |
| Do- | 1 | 8 | | | 68 |
| decyl- | 2 | 6 | | | 67 |
| sulfate | 3 | 5 | | | 69 |
| | 4 | 4 | | | 67 |
| Blank | 1 | | 4 | 9 | 4 |
| Value | 2 | | 3 | 1 | 0 |
| | 3 | | 0 | 0 | 0 |

Although the method according to the invention has been described in detail by way of the recovery of thrombin from prothrombin, the skilled artisan will understand that similar cleavages of proenzymes other than prothrombin may be carried out in an analogous manner; in this way, it is, e.g., possible to recover plasmin from plasminogen or to recover activated blood coaguation factors from their proenzymes.

What I claim is:

1. A method of proteolytically cleaving prothrombin by treatment with a protease, wherein the improvement comprises carrying out said treatment in the presence of a detergent or a chaotropic substance, wherein said chaotropic substance is selected from the group consisting of urea, guanidinium hydrochloride and a thiocyanate salt, and said protease treatment produces thrombin.

2. The method of claim 1, wherein said prothrombin is immobilized on a solid carrier material.

3. The method of claim 2, wherein said solid carrier material is a slightly soluble salt or a chelate of a bivalent metal.

4. The method of claim 3, wherein said bivalent metal is an alkaline earth metal.

5. The method of claim 1, wherein said detergent is selected from the group consisting of deoxycholate, dodecylsulfate, CHAPS, Brij ®, Tween ®, Triton ® and Pluronic ®.

6. The method of claim 1, wherein said protease is selected from the group consisting of trypsin, chymotrypsin, kallikrein, dispase and the endoproteinases Glu-C, Lys-C and Asp-N.

7. A method of purifying thrombin, comprising the steps of:
(a) providing a prothrombin-containing solution;
(b) contacting said prothrombin-containing solution with a solid carrier to obtain prothrombin immobilized on said carrier;
(c) treating said immobilized prothrombin with a protease in the presence of a detergent to obtain a thrombin-containing solution;
(d) separating said carrier from said thrombin-containing solution of step (c);
(e) isolating thrombin from said thrombin-containing solution of step (d); and (f) purifying said isolated thrombin to homogeneity to obtain pure thrombin.

8. The method of claim 7, wherein said solid carrier is a slightly soluble salt or a chelate of a bivalent metal.

9. The method of claim 8, wherein said bivalent metal is an alkaline earth metal.

10. The method of claim 9, wherein said protease is trypsin.

11. The method of claim 10, wherein said detergent is deoxycholate.

12. A method of producing a pharmaceutical preparation containing thrombin, comprising the steps of:
   (a) obtaining pure thrombin according to the method of claim 7; and
   (b) adding a pharmaceutically acceptable carrier to said pure thrombin.

* * * * *

UNITED STATES PATENT AND TRADEMARK OFFICE
CERTIFICATE OF CORRECTION

PATENT NO. : 5,432,062
DATED : July 11, 1995
INVENTOR(S) : Peter Turecek

It is certified that error appears in the above-indentified patent and that said Letters Patent is hereby corrected as shown below:

Title page, item [30] under "Foreign wherein "[AU] Australia" should read -- [AT] Austria--.

Signed and Sealed this

Twelfth Day of December, 1995

Attest:

BRUCE LEHMAN

Attesting Officer

*Commissioner of Patents and Trademarks*